United States Patent [19]

Morgan et al.

[11] Patent Number: 5,680,864

[45] Date of Patent: Oct. 28, 1997

[54] METHOD FOR PROCESSING EVENT DATA USING A REMOVABLE DATA STORAGE MEDIUM AND CLOCK

[75] Inventors: Carlton B. Morgan, Bainbridge Island; Clinton Cole, Seattle; Daniel J. Powers, Issaquah, all of Wash.

[73] Assignee: Heartstream, Inc., Seattle, Wash.

[21] Appl. No.: 703,433

[22] Filed: Aug. 26, 1996

Related U.S. Application Data

[62] Division of Ser. No. 691,975, Aug. 2, 1996, which is a continuation of Ser. No. 314,395, Sep. 28, 1994, Pat. No. 5,549,115.

[51] Int. Cl.$^6$ ............................................. A01B 5/04
[52] U.S. Cl. ............................................. 128/696
[58] Field of Search ............................................. 128/696, 697, 128/710

[56] References Cited

U.S. PATENT DOCUMENTS

| | | |
|---|---|---|
| 4,250,888 | 2/1981 | Grosskopf. |
| 4,610,254 | 9/1986 | Morgan et al.. |
| 4,715,385 | 12/1987 | Cudahy et al.. |
| 4,945,477 | 7/1990 | Edwards. |
| 5,002,062 | 3/1991 | Suzuki. |
| 5,228,450 | 7/1993 | Sellers. |
| 5,277,188 | 1/1994 | Selker. |
| 5,333,616 | 8/1994 | Mills et al.. |
| 5,334,030 | 8/1994 | Brilliott. |
| 5,338,210 | 8/1994 | Beckham et al.. |
| 5,345,367 | 9/1994 | Pierce et al.. |

OTHER PUBLICATIONS

U.S. Patent Application No. 08/227,553, "Electrotherapy Method and Apparatus" filed Apr. 14, 1994.
U.S. Patent Applicaction No. 08/240272 "Defibrillator with Self-Test Features" filed May 10, 1994.

Brochure, Advanced EMS Defibrillators from Zoll.

Operating instructions for Laerdal Heartstart Medical Control Unit with Multiplex Tape Format.

Operating instructions for Laerdal Heartstart Database Manager 3.3 (1991).

Marquette® Responder™ 1500 Defibrillator and cardiac care system operator's manual (16th Ed.) (1994).

Physio Control ECG/Voice Translator Operating Instructions.

Physio Control Code-Stat™ data management system User Guide (1996).

*Primary Examiner*—William E. Kamm
*Attorney, Agent, or Firm*—James R. Shay; Cecily Anne Snyder

[57] ABSTRACT

A method for gathering event data using a data gathering instrument having an instrument clock and an instrument data storage medium, the method comprising the steps of: gathering event data using the data gathering instrument; storing the event data in an instrument data storage medium; using an instrument clock to associate time information with the event data; storing the associated time information in the instrument data storage medium; separating the instrument data storage medium from the data gathering instrument; separating the instrument clock from the data gathering instrument; and storing in a main data storage medium the event data and the time information stored in the instrument data storage medium. The invention also includes a data gathering system practicing this method, the data gathering instrument itself, and removable instrument clock and memory modules, preferably disposed together in a housing such as a PCMCIA format card.

7 Claims, 3 Drawing Sheets

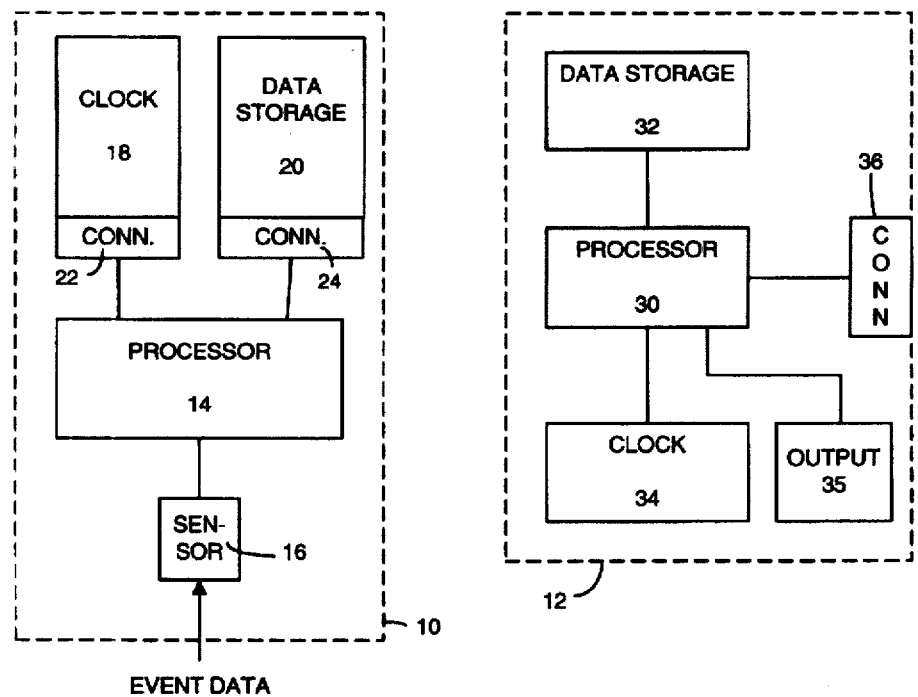
*Figure 1*
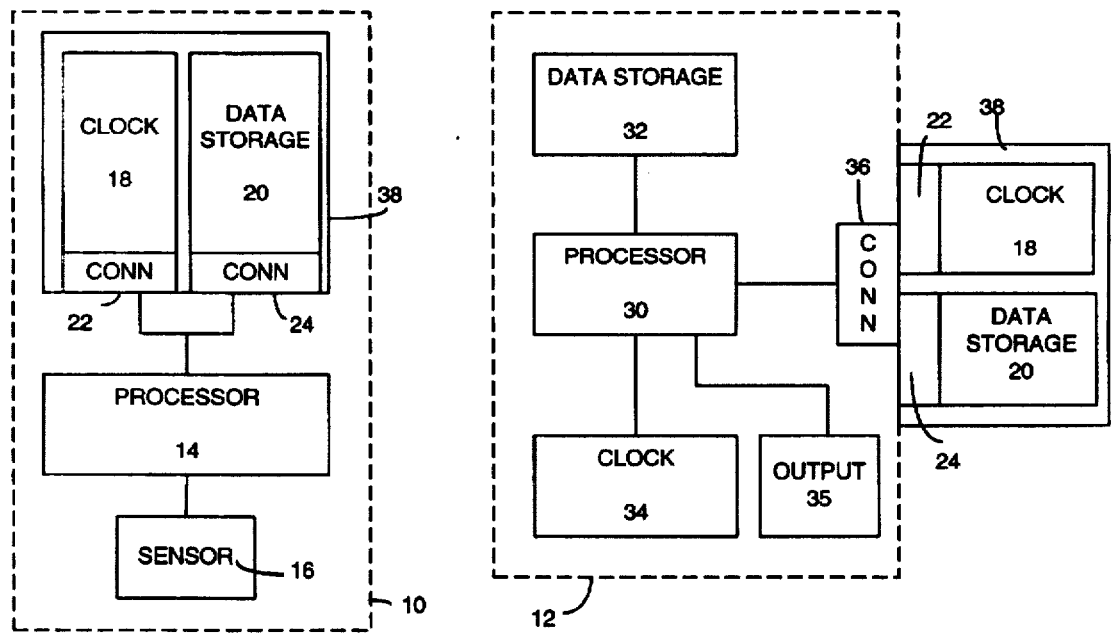
*Figure 2*                    *Figure 3*

METHOD FOR PROCESSING EVENT DATA USING A REMOVABLE DATA STORAGE MEDIUM AND CLOCK

This application is a divisional of application Ser. No. 08/691,975 filed 2 Aug. 1996, which is a continuation of application Ser. No. 08/314,395 filed 28 Sep. 1994, now U.S. Pat. No. 5,549,115.

BACKGROUND OF THE INVENTION

This invention relates to a method and apparatus for gathering event data using a removable data storage medium and clock. The invention also relates to a removable storage medium incorporating a clock for use in gathering event data.

Event data means information that can be related to particular intervals of time. The time intervals may be "elapsed time," i.e., time related to a reference event, such as power-up of the data collecting device or start of the data collection process. The time intervals may instead be synchronized with a master standard, such as Greenwich mean time or an arbitrarily selected timekeeper, in which case the time is known as "synchronized time." Accepted time units (seconds, minutes, etc.) are used to measure both elapsed time and synchronized time.

One example of event data is vehicular traffic flow information sampled on a given street, which may be plotted with respect to synchronized time (e.g., time of day in hours and minutes) over the course of a day or week. Another example of event data is an electrocardiograph showing a patient's heart electrical activity, which may be plotted versus elapsed time from a starting or triggering event. Event data also includes the raw data upon which the plots or graphs are based, whether in digital, analog or any other form. The event data may be a continuous data stream, a discontinuous series of events, or a combination of continuous data and discrete events.

Data logging is one way of gathering event data. In data logging, a data gathering instrument monitors a process or situation and gathers and stores information about the process or situation for later analysis or archiving. During subsequent analysis, it may be important to determine the relationship of the recorded events and the time of the events' occurrence. For this reason, data loggers usually have a way of annotating the collected data with the time of collection.

For example, in an industrial chemical process, reaction temperatures may be recorded by a data logger continuously for quality assurance purposes to determine whether the temperatures stayed within predetermined bounds during the reaction. If the chemical reaction temperature did exceed expected limits, a time reference permits later analysis to determine when it did so, and for how long, to help identify the necessary remedial action. To illustrate: The data logger could note either (1) that the chemical process exceeded its temperature parameters 17.3 minutes from time the reaction data logging began (i.e., the data logger is measuring elapsed time) or (2) that the reaction began at 4:30:00 PM and the excursion occurred at 4:47:20 PM (i.e., the data logger is measuring synchronized time). In both scenarios, the temperature excursion of the monitored chemical process can be related to other events going on in the chemical plant.

As another example, in may be desirable to record highway traffic for road utilization analysis. Unattended data recorders my be used to note the passage of vehicles as time series of events that can later be analyzed when the recording is recovered from the monitoring site. A time stamp for each event allows later reconstruction and analysis of traffic flow. Elapsed time data can be used to determine the frequency of vehicle traffic. Synchronized time data can be used to correlate the traffic with other events, such as shift changes at nearby businesses.

Data logging can also occur during medical treatment and procedures. For example, emergency medical technicians delivering emergency care may use defibrillators to deliver electrical shocks to a patient's heart. Event data regarding the patient's physiological condition may be logged to provide information to later caregivers about the patient and about the care the patient received, such as the time required for the emergency medical technicians to reach the patient and the patient's response to the treatment.

As discussed above, data collected from data loggers may be analyzed to extract useful time-based information. Part of the event data analysis often requires reference to a local clock by the data user to place the time stamped on the collected event in the context of the data user's time. For example, if a portion of the collected event indicates that the event occurred at 4:00 PM, the data user must assume that the data logger clock and the data user's local clock indicated "4:00 PM" at the same time. In other words, the data user must assume that the data logger clock and the data user's local clock are synchronized. In addition, the data user must assume that the data logger's measure of a second or a minute is the same as the data user's local measure of a second or a minute so that the recorded time (whether elapsed time or synchronized time) may be interpreted in a meaningful way.

The synchronized time indicated by a data logger's clock may drift from the synchronized time indicated by the master timekeeper because of environmental conditions, mechanical problems, or other reasons. Also, the act of setting the data logger clock could introduce discrepancies between the time indicated by the data logger clock and the time indicated by the data user's clock, especially if the data logger clock is set by hand, or if the data logger's clock was not initially synchronized to the data user's clock prior to event data collection. These problems are compounded if a single data user receives event data from multiple data loggers, since each data logger clock my have been affected in different ways by environmental conditions, errors in initial setting, and the like. Thus, when the accurate logging of synchronized time is important, a relatively expensive clock and elaborate and/or expensive time setting procedures may have to be included in the data logger.

SUMMARY OF THE INVENTION

This invention is a method and apparatus that overcomes some of the shortcomings of prior art event data logging methods and apparatuses. According to this invention, the clock used by the data logger or data gathering instrument is compared to a main clock associated with a main data repository. The invention eliminates time recording errors introduced by referencing the data gathering instrument clock to an external time standard that might differ from a data user's clock. In addition, since the data gathering instrument clock is periodically compared to a main clock, any errors in the instrument clock can be identified and corrected. Thus, a less accurate, and therefore less expensive, clock may be used in the data gathering instrument.

The preferred embodiment of the invention is a method for gathering event data using a data gathering instrument having an instrument clock and an instrument data storage medium, the method comprising the steps of: gathering event data using the data gathering instrument; storing the event data in an instrument data storage medium; using an instrument clock to associate time information with the event data; storing the associated time information in the instrument data storage medium; separating the instrument data storage medium from the data gathering instrument; separating the instrument clock from the data gathering instrument; and recovering in a main data recovery unit the event data and the time information stored in the instrument data storage medium. The invention also includes a data gathering system practicing this method, the data gathering instrument itself, and removable instrument clock and memory modules, preferably disposed together in a housing such as a PCMCIA format card.

In other embodiments, the invention includes multiple data gathering instruments used together with a single data recovery unit in a data gathering system.

The main data recovery unit may include a data storage medium for storing data received from a data gathering unit; an output such as a display for the data received from a data gathering instrument and/or stored in the recovery unit's data storage medium; and a processor for analyzing the data from one or multiple data gathering instruments.

The main data recovery unit may synchronize the clock of a data gathering instrument with the main clock in the recovery unit. The main data recovery unit may also correct for drift or other time errors in the data gathering instrument clock.

The data gathering instrument may gather event data at a location that is physically distant from a central data recovery unit that may be located in a primary care facility. In a preferred embodiment, the data gathering instrument is a defibrillator. The event data gathered by the defibrillator may include patient ECG data, defibrillator operating condition data, and ambient voice data.

The invention is described in more detail below with reference to the drawings.

BRIEF DESCRIPTION OF THE DRAWINGS

FIG. 1 is a schematic block diagram showing a data gathering system according to this invention.

FIG. 2 is a schematic block diagram of a data gathering instrument according to one embodiment of this invention.

FIG. 3 is a schematic block diagram of a main data repository to which an instrument data module and an instrument clock module have been attached.

DETAILED DESCRIPTION OF THE PREFERRED EMBODIMENTS

Figure 4:
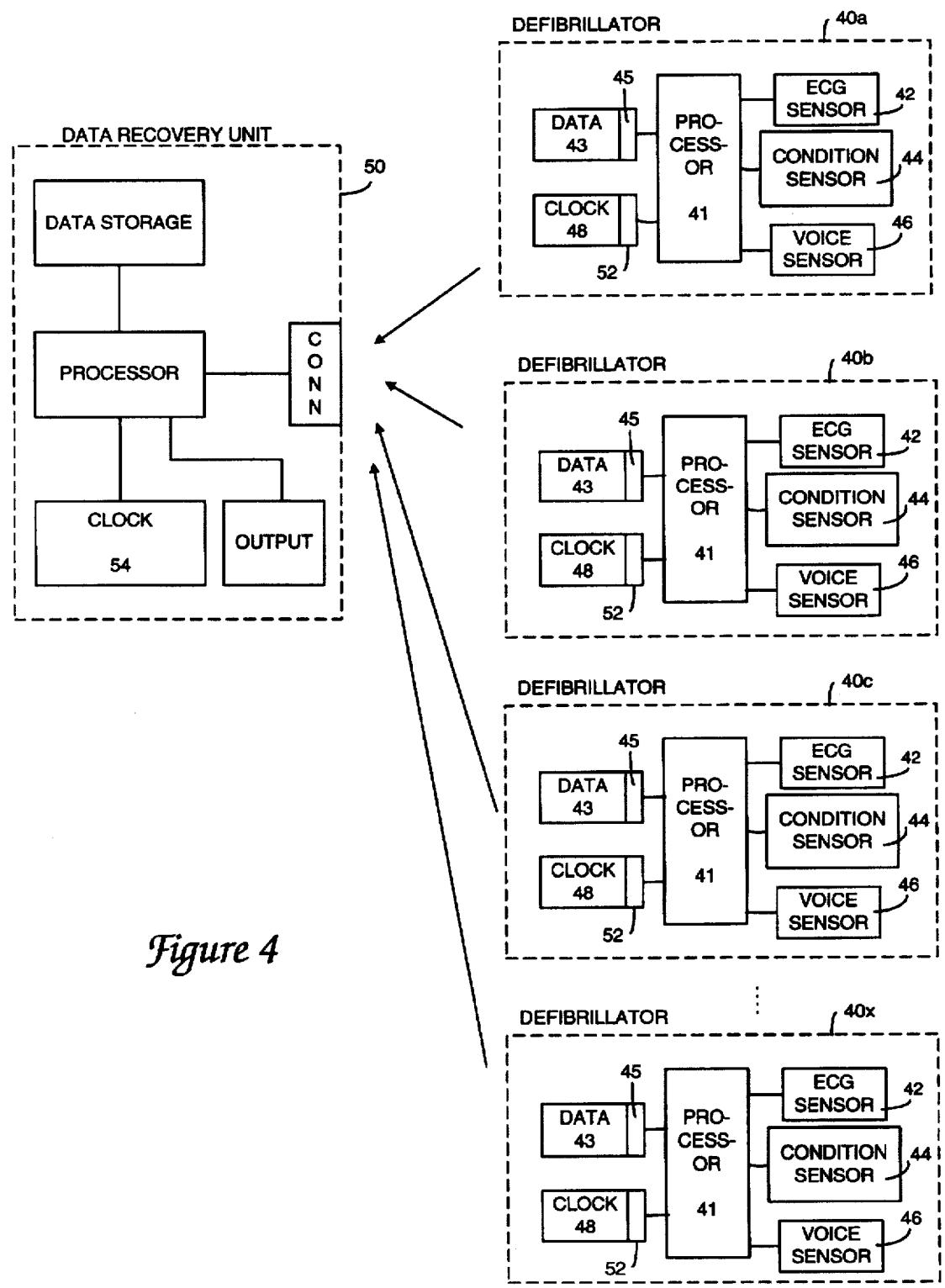
FIG. 4 is a schematic block diagram of a data gathering system according to this invention.

FIG. 1 shows a data gathering system according to a preferred embodiment of this invention. The system has two main components: a data gathering instrument 10 and a main data recovery unit 12. The data gathering instrument 10 has a processor or controller 14 which interacts with at least one sensor or data gathering element 16, a removable clock 18 and a removable data storage medium 20. Clock 18 has a connector 22 for communicating clock information to and from the clock, and together the clock 18 and its connector 22 form a removable clock module. Likewise, the data storage medium 20 has a connector 24 for communicating data information to and from the data storage medium, and together the data storage medium 20 and its connector 24 form a removable data storage module.

The purpose of the main data recovery unit is to receive data from one or more data gathering instruments for data storage, display and/or analysis. Main data recovery unit 12 includes a processor 30 communicating with an optional main data storage medium 32, a main clock 34, an output 35 such as a display, and a recovery unit connector 36. Connector 36 is designed to mate with clock module connector 22 so that clock information can be communicated between the clock module and the processor, as shown schematically in FIG. 3. Connector 36 is also designed to mate with data storage module connector 24 so that data can be communicated between the data storage module and the main data recovery unit, as shown schematically in FIG. 3.

FIG. 2 shows an alternative embodiment of the data gathering instrument in which the data storage module and the clock module are physically connected, such-as by being disposed in a coercion housing 38. Other ways of connecting the two modules are possible, of course, without departing from the scope of the invention. In this embodiment, connectors 22 and 24 may be part of a single connector, as shown schematically in FIG. 2. In any event, as in the FIG. 1 embodiment the connectors mate with connector 36 of the main data recovery unit to communicate data and clock information, as shown schematically in FIG. 3.

In use, the data gathering instrument 10 gathers event data using its sensor 16. The characteristics of the event data (e.g., discrete data versus continuous data) and the manner in which the event data is gathered by the instrument are dependent on the type of data gathering instrument being used and form no part of this invention. The event data is stored in data storage medium 20. Likewise, clock 18 generates time data associated with the event data. The time data requirements (e.g., elapsed time versus synchronized time) are dependent on the type of event data being gathered and the type of data gathering instrument being used and form no part of this invention. The time data is also stored in data storage medium 20.

After gathering event data and generating time data, the instrument clock 18 and data storage medium 20 are separated from the data gathering instrument 10 and associated with the main data recovery unit 12, such as through connectors 22, 24 and 36 on the instrument clock 18, instrument data storage medium 20 and main data recovery unit 12, respectively. The event data and time data are transferred or copied from the instrument data storage medium 20 to the main data recovery unit for storage in main data storage medium 32, for display on output 35 and/or analysis in processor 30.

Connection of the instrument clock 18 with the main data recovery unit 12 through their respective connectors permits the main data recovery unit to compare the time indicated by the instrument clock 18 with the time indicated by the main clock 34. If this step is performed without any prior synchronization, the comparison will indicate the reliability of any synchronized time data associated with the event data stored in the instrument data storage medium. If, however, the instrument clock had been earlier synchronized with the main clock, the later comparison of the times indicated by the two clocks would permit the main data recovery unit processor to correct any discrepancies (e.g., time drift) in the stored time data, for example through a simple interpolation routine. Discrepancies between the data recovery unit clock and the data gathering instrument clock can be corrected without prior synchronization, of course, if the data gathering clock drift rate is known or can be measured or otherwise determined.

The method is simplified, of course, if the instrument data storage medium 20 and the instrument clock 18 are physically connected, such as, for example, by a housing 38. In that case the separation of data storage medium 20 and clock 18 from the data gathering instrument occurs substantially simultaneously. In addition, physical connection of the two elements will help assure that the main data recovery unit will correctly associate the event and time data with the clock that provided the time data.

The data gathering systems shown in FIGS. 1-3 are particularly useful as part of a larger data gathering system that has multiple data gathering instruments collecting event data to be later transferred or copied to a single main data recovery unit. The data gathering instruments may be physically distant from the main data recovery unit, at least for the time during which the event data is gathered. After the event data has been gathered, the individual instrument data storage mediums and instrument clocks may be moved to the location of the main data recovery unit, either before or after the data storage mediums and clocks have been separated from their respective data gathering instruments.

The following example illustrates the invention. It is not intended to limit the invention in any way. In this example, the data gathering instrument is a defibrillator. A defibrillator is a therapeutic device that may be used to deliver an electrical shock to a patient's heart to correct an irregular rhythm such as ventricular fibrillation. Further details about defibrillators and defibrillation may be found in U.S. patent application Ser. No. 08/227,553, "Electrotherapy Method and Apparatus," filed Apr. 14, 1994, and U.S. patent application Ser. No. 08/240,272, "Defibrillator With Self-Test Features," filed May 10, 1994, the disclosures of which are incorporated herein by reference.

In addition to providing the electrical shock, a defibrillator may also collect physiological information from the patient, such as an ECG (electrocardiogram) signal of the electrical activity of the patient's heart over the course of the monitoring time. This event data may be stored by the defibrillator for later use by medical personnel in the diagnosis and treatment of the patient. In addition, event data relating to the operation of the defibrillator (e.g., capacitor voltage during charging and discharging or the time at which shocks were delivered) and even event data consisting of the voices of the assisting medical personnel may be recorded for later use.

Defibrillators may be deployed on emergency medical vehicles for use in the field by medical personnel. Event data collected by the defibrillators may be used later in a location, such as a hospital, which is physically distant from the initial treatment location. With reference to FIG. 4, according to this invention, a defibrillator data storage medium 43 containing the event data collected by the defibrillator 40a through its ECG sensor 42, defibrillator condition sensor 44 and voice sensor 46 through the operation of processor 41 can be separated from the defibrillator and connected to a main data recovery unit 50 (such as a computer) in the hospital or other location through appropriate connectors 45 and 52. In this way, the event data is available for later diagnosis and treatment, and the defibrillator itself remains available for use in the field.

Also, the instrument clock 48 used by the defibrillator to associate time information with the ECG, voice, defibrillator operating condition, and/or other event data can be separated from the defibrillator as well and connected to the main data recovery unit along with the data storage medium. This step permits a comparison between the instrument clock 48 and a main clock 54 within the main data recovery unit so that the defibrillator event data can be associated with synchronized time. This comparison can be used to determine whether synchronized time indicated by the instrument clock (i.e., the time associated with the recorded event data) differs from the synchronized time standard shown by the main data recovery unit. In addition, the ability to connect the instrument clock and the main clock permits synchronization of the defibrillator clock prior to use in the field and correction for any instrument clock drift after use in the field through interpolation or any other known technique.

Furthermore, this system permits multiple defibrillators to synchronize their instrument clocks with a single main clock and to transfer or copy their collected event data into a single data recovery unit. Thus, as shown schematically in FIG. 4, multiple substantially identical defibrillators 40a–40x can gather event data at locations remote from a central data recovery unit. The event data gathered by each will eventually be recovered in a single place and will be synchronized to a single time source.

Each data gathering instrument may uniquely identify the data it gathers so that the main data recovery unit will be able to distinguish event data gathered from one instrument from other event data. This data identification may be done in any manner known in the art.

This invention can be used to learn valuable information regarding emergency medical response times. Since the instrument clocks are each synchronized to the clock in the main data recovery unit, the main data recovery unit can accurately calculate the time between dispatch (if the dispatch clock is synchronized to the main data recovery unit clock) and use of the defibrillator to treat the patient. The calculated response times for each defibrillator can be accurately compared, since each defibrillator clock is synchronized to the same recovery unit clock. The invention also eliminates the need for a technician to periodically set a reference time source (such as his or her watch) from the main clock and visit all of the remote defibrillator sites in order to keep all of the instrument clocks in the system synchronized.

Figure 5:
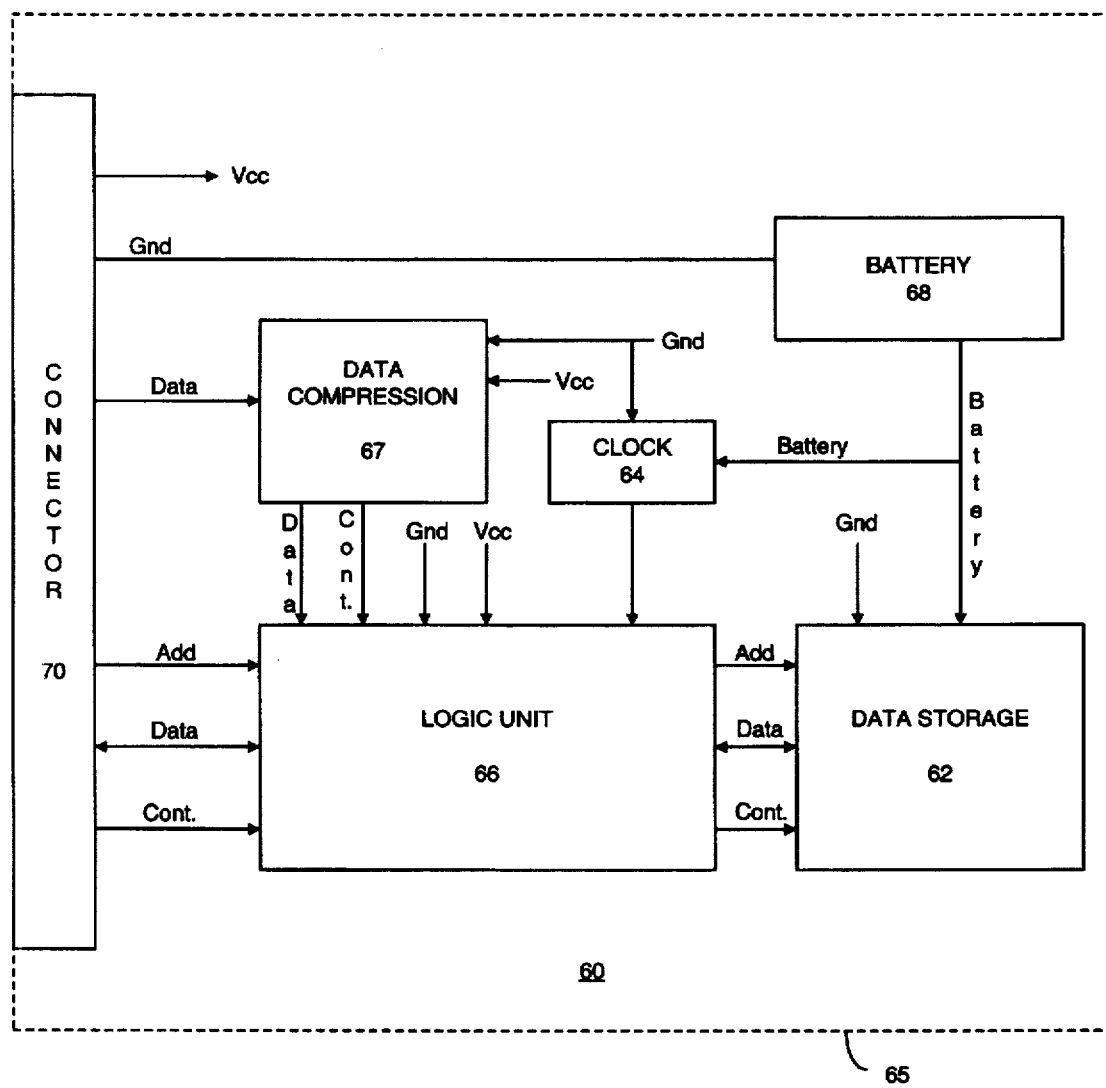
FIG. 5 is a schematic block diagram of an event data storage apparatus for use with a data gathering instrument.

The preferred embodiment of an instrument data storage medium and instrument clock is shown in FIG. 5. This embodiment can be used, for example, in a defibrillator as discussed above. In this embodiment, the instrument data storage medium and instrument clock are both disposed in a package conforming to Personal Computer Memory Card International Association (PCMCIA) Release 2.1 standard. Information regarding this standard and details about the construction of PCMCIA cards and their interfacing connectors may be found in U.S. Pat. No. 5,334,030; U.S. Pat. No. 5,345,367; U.S. Pat. No. 5,338,210; and PCMCIA Standards, release 2 (Nov. 1992); the disclosures of which are incorporated herein-by reference.

FIG. 5 is a schematic representation of the components of the combination data storage medium 62 and instrument clock 64 arranged on a circuit board 60 within the PCMCIA housing 65. Data storage medium 62 may be any suitable digital medium, such as flash memory or static RAM, with the memory storage capacity dictated by the application. Clock 64 is preferably an oscillator whose frequency also depends on the application.

A logic unit 66, such as an ASIC, controls the clock 64 and the event data going to and coming from data storage medium 62. An optional data compression chip 67 may also be provided to compress some or all of the data stored in medium 62, such as voice data. A power source 68, such as a lithium battery, provides power (as necessary) to the data storage medium 62 and clock 64. Communication between the PCMCIA card and any device to which the card is connected is through a card connector 70, as is known to those familiar with PCMCIA cards. Communication within the PCMCIA card is accomplished via suitable communication channels or buses, as is also known in the art.

The following is a summary of the use of the method of this invention as applied to a data gathering system consisting of two or more mobile defibrillators and a single central data recovery unit located within a primary care facility. This description assumes that the defibrillators' instrument clock modules and data storage modules are configured in a PCMCIA card format such as the one described above. It should be understood, however, that other clock and data storage module designs fall within the scope of this invention.

An emergency medical vehicle carrying a defibrillator is dispatched from the primary care facility in response to a call for assistance. The dispatch time for each be noted in some manner. When it is deployed by medical personnel, the defibrillator begins gathering and storing event data and the synchronized time associated with the event data. As discussed above, the event data my include defibrillator operating condition, patient ECG and ambient voice data. After treatment, the PCMCIA card containing the stored event data and a defibrillator instrument clock is removed from the defibrillator and inserted into the central data recovery unit (e.g., the computer).

The computer can extract the event data from the PCMCIA card data storage medium for analysis, display, and/or storage in the computer or in an associated peripheral data storage device. The analysis could possibly include calculation of time from dispatch to first shock; response of the patient's ECG to the shock; and correlation of voice data information (e.g., descriptions of the patient's condition spoken aloud by the attending medical personnel) with the ECG and defibrillator operating condition data.

In addition, the computer can compare the defibrillator instrument clock with the computer's own main clock to determine whether the recorded defibrillator synchronized times should be corrected for drift and to perform the correction as described above. The time-corrected data can thus be used to acquire accurate care delivery system performance information useful for quality assurance.

The invention includes modifications to the embodiments described above. For example, the data storage medium used in either the data gathering instrument or in the data recovery unit can be any suitable digital or analog medium. Also, formats other than the PCMCIA format for the instrument clock and instrument data storage may be used. Neither the instrument data storage medium and its connector nor the instrument clock and its connector need be arranged as a single module. In fact, connectors need not be used at all if some other means of information transfer (e.g., IR or RF transmission) is used. In addition, while defibrillators are described in detail above, this invention may be adapted to any data gathering instrument.

Other modifications will be apparent to those skilled in the art.

We claim:

1. A method for processing event data comprising the following steps:

gathering event data using a defibrillator;

storing the event data in a data storage medium disposed within an event data storage apparatus housing, the event data storage housing being connected to the defibrillator;

obtaining time information from an event data clock disposed in the event data storage apparatus housing; and storing the time information in the data storage medium.

2. The method of claim 1 further comprising disconnecting the event data storage housing from the defibrillator.

3. The method of claim 2 further comprising recovering in a main data recovery unit the event data and the time information stored in the data storage medium.

4. The method of claim 1 wherein the housing comprises a PCMCIA format card housing.

5. The method of claim 1 further comprising calculating time between an external event and use of the defibrillator to treat a patient.

6. The method of claim 5 wherein the external event is dispatch of the defibrillator to treat a patient.

7. The method of claim 1 further comprising synchronizing a dispatch clock with a clock in the main data recovery unit.

* * * * *